US012373978B2

United States Patent
Lee

(10) Patent No.: US 12,373,978 B2
(45) Date of Patent: Jul. 29, 2025

(54) INTRAORAL IMAGE PROCESSING APPARATUS, AND INTRAORAL IMAGE PROCESSING METHOD

(71) Applicant: MEDIT CORP., Seoul (KR)

(72) Inventor: Ho Taik Lee, Seoul (KR)

(73) Assignee: MEDIT CORP., Seoul (KR)

( * ) Notice: Subject to any disclaimer, the term of this patent is extended or adjusted under 35 U.S.C. 154(b) by 446 days.

(21) Appl. No.: 17/726,798

(22) Filed: Apr. 22, 2022

(65) Prior Publication Data

US 2022/0343528 A1    Oct. 27, 2022

(30) Foreign Application Priority Data

Apr. 23, 2021 (KR) .................. 10-2021-0053120

(51) Int. Cl.
*G06T 7/64* (2017.01)
*G06T 7/90* (2017.01)

(52) U.S. Cl.
CPC .................. *G06T 7/64* (2017.01); *G06T 7/90* (2017.01); *G06T 2207/20216* (2013.01); *G06T 2207/20224* (2013.01); *G06T 2207/30036* (2013.01)

(58) Field of Classification Search
CPC ... G06T 7/64; G06T 7/90; G06T 2207/20216; G06T 2207/20224; G06T 2207/30036; G06T 2207/10068; G06T 1/0007; G06T 17/00; A61B 1/000094; A61B 1/24; A61B 5/0088; A61B 5/7445; A61B 6/52; A61B 6/512; A61C 9/0046; G16H 30/00; G16H 50/50

See application file for complete search history.

(56) References Cited

U.S. PATENT DOCUMENTS

| | | | |
|---|---|---|---|
| 2004/0029068 A1* | 2/2004 | Sachdeva | G16H 50/50 433/24 |
| 2011/0038514 A1* | 2/2011 | Weigl | A61C 9/0053 382/128 |

OTHER PUBLICATIONS

Guillaume Lavoue , "A local roughness measurer 3D meshes and its application to visual masking", publication date: Jan. 2009. (Year: 2009).*

Rusinkiewicz S, "Estimating curvatures and their derivatives on triangle meshes", 3D Data Processing, Visualization and Transmission, 2004. 3DPVT 2004. Proceedings. 2nd International Symposium on Thessaloniki, Greece Sep. 6-9, 2004, Piscataway, NJ, USA, IEEE, (Sep. 6, 2004), pp. 486-493 (8 pages total) XP010725250.

(Continued)

*Primary Examiner* — Mekonen T Bekele
(74) *Attorney, Agent, or Firm* — Sughrue Mion, PLLC

(57) ABSTRACT

Provided are an intraoral image processing method and an intraoral image processing apparatus. The intraoral image processing method according to an embodiment may include: obtaining a three-dimensional oral cavity model of (Continued)

an oral cavity; obtaining curvature information of the three-dimensional oral cavity model; obtaining roughness information of the three-dimensional oral cavity model, based on the curvature information; obtaining a color of the three-dimensional oral cavity model, based on the roughness information; and displaying the three-dimensional oral cavity model, based on the obtained color.

18 Claims, 11 Drawing Sheets

(56) References Cited

OTHER PUBLICATIONS

Kushunapally Rakesh et al, "Roughness as a Shape Measure", Computer-Aided Design and Applications, vol. 4, No. 1-4, doi:10.1080/16864360.2007.10738550, (Jan. 1, 2007), pp. 295-310 (16 pages total) URL: http://www.cad-journal.net/files/vol_4/CAD_4(1-4)_2007_295-310.pdf, XP055966386.
Chang Ha Lee et al, "Mesh saliency", Jul. 1, 2005; 1077952576-1077952576, (Jul. 1, 2005), doi:10.1145/1186822.1073244, pp. 659-666 (8 pages total) XP058335221.
Guillaume Lavoue et al, "Perceptually driven 3D distance metrics with application to watermarking", Spie Proceedings, US, (Aug. 24, 2006), vol. 6312, doi:10.1117/12.686964, ISBN 978-1-5106-3673-6, p. 63120L (13 pages total) XP055709954.
Meyer M et al, "Discrete Differential-Geometry Operators for Triangulated 2-Manifolds", International Workshop on Visualization and Mathematics, XX, XX, (May 22, 2002), pp. 1-26 (26 pages total)XP002978988.
Dong Chen-Shi et al, "Curvatures estimation on triangular mesh", Journal of Zhejiang University Science A, Zheijiang University Press, CN, vol. 6, No. 1, doi:10.1007/BF02887228, ISSN 1673-565X, (Aug. 1, 2005), pp. 128-136 (9 pages total) (Aug. 1, 2005), XP036040004.
Guillaume Lavoue, "A local roughness measure for 3D meshes and its application to visual masking", ACM Transactions on Applied Perception, Association for Computing Machinery, Inc, New York, NY, US, (Feb. 3, 2009), vol. 5, No. 4, doi:10.1145/1462048.1462052, ISSN 1544-3558, pp. 1-23 (23 pages total) XP058355893.
Extended European Search Report dated Oct. 18, 2022 in Application No. 22169560.4.
Office Action dated Dec. 20, 2022 from the Korean Patent Office in Application No. 10-2021-0053120.

\* cited by examiner ions of the three-dimensional oral cavity model, based on the curvature information may include obtaining roughness values of the pointes, based on the curvature values of the points.
INTRAORAL IMAGE PROCESSING APPARATUS, AND INTRAORAL IMAGE PROCESSING METHOD

CROSS-REFERENCE TO RELATED APPLICATION

This application claims the benefit of Korean Patent Application No. 10-2021-0053120, filed on Apr. 23, 2021, in the Korean Intellectual Property Office, the disclosure of which is incorporated herein in its entirety by reference.

BACKGROUND

1. Field

The disclosure relates to an intraoral image processing apparatus and method, and more particularly, to an apparatus and method of processing an intraoral image to provide roughness information about a three-dimensional oral cavity model.

2. Description of the Related Art

Recently, a method of obtaining an image of an oral cavity of a patient by inserting an intraoral scanner into the oral cavity has been used as a method of obtaining oral cavity information of the patient. By scanning the patient's oral cavity by using an intraoral scanner, three-dimensional data about an object such as the patient's tooth, gum, jawbone, and the like may be obtained, and the obtained three-dimensional data is used for treatment, correction, or the like of a tooth.

In particular, in order to place a prosthesis on a tooth, a tooth serving as a support for a prosthesis is cut into the shape of an abutment, and the prosthesis is capped over the cut tooth. In this state, to smoothly cut the tooth serving as a prosthesis support, information about roughness of the tooth is necessary. However, in technologies for obtaining roughness with respect to scan data according to the related art, as tooth-specific geometric information is not considered, it is difficult for the technologies to be applied to an oral cavity model.

SUMMARY

Provided is an intraoral image processing apparatus and method capable of providing roughness information about a three-dimensional oral cavity model.

Additional aspects will be set forth in part in the description which follows and, in part, will be apparent from the description, or may be learned by practice of the presented embodiments.

According to an aspect to the disclosure, an intraoral image processing method includes obtaining a three-dimensional oral cavity model of an oral cavity, obtaining curvature information of the three-dimensional oral cavity model, obtaining roughness information of the three-dimensional oral cavity model, based on the curvature information, obtaining a color of the three-dimensional oral cavity model, based on the roughness information, and displaying the three-dimensional oral cavity model, based on the obtained color.

In an embodiment, the obtaining of the curvature information of the three-dimensional oral cavity model may include obtaining curvature values of points included in the three-dimensional oral cavity model, and the obtaining of the roughness information of the three-dimensional oral cavity model, based on the curvature information may include obtaining roughness values of the pointes, based on the curvature values of the points.

In an embodiment, the obtaining of the roughness values of the points may include determining a roughness value of a first point, based on a curvature value of at least one second point adjacent to the first point among the points.

In an embodiment, the obtaining of the roughness values of the points may include determining a roughness value of a first point, based on a value of a difference between a curvature value of at least one second point adjacent to the first point among the points and a curvature value of the first point.

In an embodiment, the obtaining of the roughness values of the points may include calculating a value of a difference between a curvature value of each of second points located within a preset first distance from a first point among the points and a curvature value of the first point, determining a weight of the difference value, based on a distance between the first point and each of the second points, and determining a roughness value of the first point, based on the difference values and the weights with respect to the second points.

In an embodiment, the determining of the roughness value of the first point may include calculating an average value of the difference values, based on the weights, and determining the calculated average value as a roughness value of the first point.

In an embodiment, the obtaining of the roughness values of the points may include determining the roughness values of the points such that roughness values of the points increase as surfaces of the three-dimensional oral cavity model on which the points are located become increasingly rough, and roughness values of the points decrease as the surfaces of the three-dimensional oral cavity model on which the points are located become increasingly smooth.

In an embodiment, the obtaining of the roughness values of the points may further include determining roughness values of points included in an edge region of a tooth or a teethridge region to be preset values.

In an embodiment, the obtaining of the roughness value of the first point may include determining whether the first point is included in an edge region of a tooth or a teethridge region, based on a distance between a tangent line of the first point and each of a third point farthest from the first point in a first direction and a fourth point farthest from the first point in a second direction among points located within a preset second distance from the first point, and when the first point is included in the edge region of the tooth or the teethridge region, determining the roughness value of the first point to be a preset value.

In an embodiment, the obtaining of the color of the three-dimensional oral cavity model may include determining a color of a point according to the roughness value of each of the points, and determining a color of a mesh constituted by the points, by mixing colors of the points.

According to another aspect of the disclosure, an intraoral image processing apparatus includes a display, a memory storing one or more instructions, and a processor, wherein the processor is configured to, by executing the one or more instructions stored in the memory, obtain a three-dimensional oral cavity model of an oral cavity, obtain curvature information of the three-dimensional oral cavity model, obtain roughness information of the three-dimensional oral cavity model, based on the curvature information, obtain a color of the three-dimensional oral cavity model, based on the roughness information, and control the display to display the three-dimensional oral cavity model, based on the obtained color.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
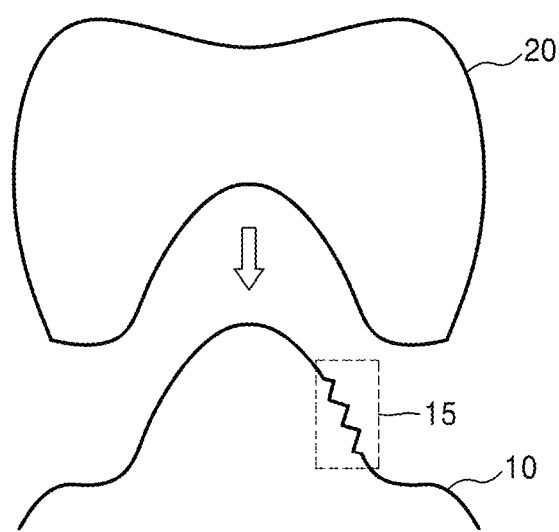
FIG. 1 is a reference view showing a prep operation according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

The present specification describes the principle of the disclosure and discloses embodiments to clarify the scope of rights of the disclosure and enable one skilled in the art to which the disclosure pertains to work the disclosure. The disclosed embodiments may be implemented in various forms.

Throughout the specification, like reference numerals denote like constituent elements. The present specification does not describe all elements of embodiments, and general matters in the technical field to which the disclosure pertains, or redundant descriptions between embodiments, are omitted. Terms such as "part" or "portion" used in the specification may be embodied by software or hardware, and according to embodiments, a plurality of "parts" or "portions" may be embodied as one unit or elements or one "part" or "portion" may include a plurality of units or elements. Hereinafter, the operation principle and embodiments of the disclosure are described with reference to the accompanying drawings.

In the present specification, an image may include an image (hereinafter, referred to as "intraoral image") representing at least one tooth or oral cavity including at least one tooth.

Furthermore, in the present specification, an image may be a two-dimensional image of an object or a three-dimensional model or three-dimensional image that represents an object in three-dimensions. Furthermore, in the preset specification, an image may mean data needed to express an object in two-dimensions or three-dimensions, for example, raw data and the like obtained from at least one image sensor. In detail, raw data is data obtained to generate an intraoral image, that is, data, for example, two-dimensional data, obtained by at least one image sensor included in an intraoral scanner when a patient's oral cavity that is an object is scanned by using an intraoral scanner. Alternatively, the raw data may be data obtained from at least one image sensor included in a table scanner when a plaster model and the like is scanned by using the table scanner. Alternatively, the raw data may be CAD data that is previously stored in an intraoral image processing apparatus. However, the disclosure is not limited thereto.

In the present specification, an "object" may include a tooth, gingiva, at least a partial region of an oral cavity, and/or an artificial structure that can be inserted into the oral cavity (for example, an orthodontic device, a prosthesis, an implant, an artificial tooth, an orthodontic auxiliary tool inserted into the oral cavity, etc.), a plaster model, an impression model, and the like. Here, the orthodontic device may include at least one of a bracket, an attachment, an orthodontic screw, a lingual orthodontic device, and a removable retainer. In the present specification, for convenience of explanation, although an object is described as an "oral cavity," embodiments of the disclosure may be identically applied not only to oral cavity, but also an artificial structure, a plaster model, an impression model, and the like that can be inserted into the oral cavity, and the oral cavity may be understood as a concept including an artificial structure, a plaster model, an impression model, and the like that can be inserted into the oral cavity.

In the following description, embodiments are described in detail with reference to the accompanying drawings.

FIG. 1 is a reference view showing a prep operation according to an embodiment.

Referring to FIG. 1, in a prosthetic treatment of placing a prosthesis 20 on a tooth 10, the tooth 10 serving as a support for the prosthesis 20 is cut in the form of an abutment. In this state, a work of cutting and trimming the tooth 10 in the form of an abutment is referred to as a prep operation, and a tooth cut in the form of an abutment is referred to as a prep tooth. When a rough part 15 exists on a surface of the prep tooth 10, and the prosthesis 20 is placed on the prep tooth 10, precise registration may not be achieved due to irregularities. Accordingly, during placing of the prosthesis 20, it is important to smoothly process the surface of the prep tooth 10 without irregularities, and a rough part is often checked after the first prep, and the second prep is repeated on the rough part, thereby performing the prep operation. In this state, in order to check the rough part 15 of the prep tooth 10, roughness information about the prep tooth 10 is necessary.

The intraoral image processing apparatus according to an embodiment may provide roughness information about a three-dimensional oral cavity model for precise performance of a prep operation. Hereinafter, a method of providing roughness information about a three-dimensional oral cavity model, which is performed by the intraoral image processing apparatus according to an embodiment, is described with reference to the accompanying drawings.

Figure 2:
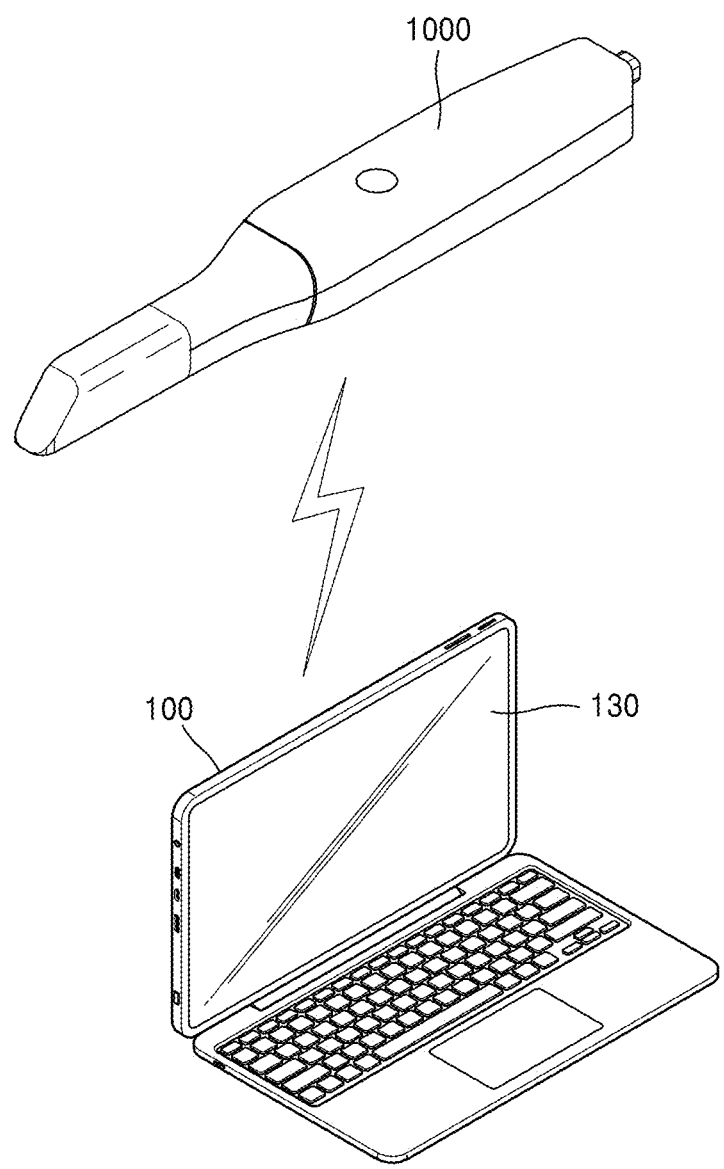
FIG. 2 illustrates an intraoral image processing system according to an embodiment.

FIG. 2 illustrates an intraoral image processing system according to an embodiment.

Referring to FIG. 2, an intraoral image processing system according to an embodiment may include an intraoral scanner 1000 and an intraoral image processing apparatus 100.

The intraoral scanner 1000 according to an embodiment is a medical apparatus for obtaining an image in an oral cavity. In detail, the intraoral scanner 1000 may be an apparatus for obtaining an image of an oral cavity including at least one tooth by being inserted into the oral cavity to scan a tooth in a non-contact manner.

Furthermore, the intraoral scanner 1000 may have a shape to be capable of being drawn in and out of an oral cavity, and scan the inside of a patient's oral cavity by using at least one image sensor, for example, an optical camera and the like. The intraoral scanner 1000 may obtain surface information about an object, as raw data, for imaging of at least one surface of a tooth, a gingiva, and an artificial structure to be inserted in the oral cavity, for example, an orthodontic device including a bracket, a wire, and the like, an implant, an artificial tooth, an orthodontic auxiliary tool inserted in an oral cavity, and the like, in a target oral cavity.

Image data obtained by the intraoral scanner 1000 may be transmitted to the intraoral image processing apparatus 100 that is connected through a wired or wireless communication network.

The intraoral image processing apparatus 100 may include a display 130. The intraoral image processing apparatus 100 may include electronic apparatuses that are connected to the intraoral scanner 1000 via a wired or wireless communication network and are capable of receiving, from the intraoral scanner 1000, a two-dimensional image obtained by scanning an oral cavity, and generating, processing, displaying, and/or transmitting an intraoral image, based on the received two-dimensional image.

The intraoral image processing apparatus 100 may generate information by processing the two-dimensional image data, or an intraoral image by processing the two-dimensional image data, based on the two-dimensional image data received from the intraoral scanner 1000. Furthermore, the intraoral image processing apparatus 100 may display the generated information and the generated intraoral image through the display 130.

The intraoral image processing apparatus 100 may include computing devices such as smart phones, laptop computers, desktop computers, PDAs, tablet PCs, and the like, but the disclosure is not limited thereto.

Furthermore, the intraoral image processing apparatus 100 may be present in the form of a server, a server device, and the like for processing an intraoral image.

Furthermore, the intraoral scanner 1000 may transmit raw data obtained through oral cavity scanning, as it is, to the intraoral image processing apparatus 100. In this case, the intraoral image processing apparatus 100 may generate a three-dimensional model (three-dimensional intraoral image) that represents an oral cavity three dimensionally, based on the received raw data. The intraoral image processing apparatus 100 according to an embodiment may generate three-dimensional data, for example, surface data, representing the shape of a surface of an object in three-dimensions, based on the received raw data.

According to an embodiment, three-dimensional surface data may be in the form of point data or mesh data. For example, mesh data is a combination of a plurality of polygons (faces), and a polygon means a polygon formed by a plurality of vertices. In this state, a polygon may be polygonal such as triangular, rectangular, and the like, and according to the shape of a polygon, mesh data may be represented as a triangular mesh, a rectangular mesh, or a polygonal mesh.

According to an embodiment, as a "three-dimensional oral cavity model" may be generated by three-dimensionally modeling an inner structure of an oral cavity, based on the received raw data, the three-dimensional oral cavity model may be referred to as a "three-dimensional intraoral image." In the following description, a model or image that represents an oral cavity two-dimensionally or three-dimensionally is collectively referred to as an "intraoral image."

Furthermore, the intraoral image processing apparatus 100 may analyze, process, display, and/or externally transmit the generated intraoral image.

In another example, the intraoral scanner 1000 may obtain raw data through the oral cavity scanning, and generate an image corresponding to a target oral cavity by processing the obtained raw data. Furthermore, the generated image may be transmitted to the intraoral image processing apparatus 100. In this case, the intraoral image processing apparatus 100 may analyze, process, display, and/or transmit the received image.

In the disclosed embodiment, the intraoral image processing apparatus 100 is an electronic apparatus capable of generating and displaying an intraoral image that three-dimensionally represents an oral cavity including one or more teeth, which is described below in detail.

Figure 3:
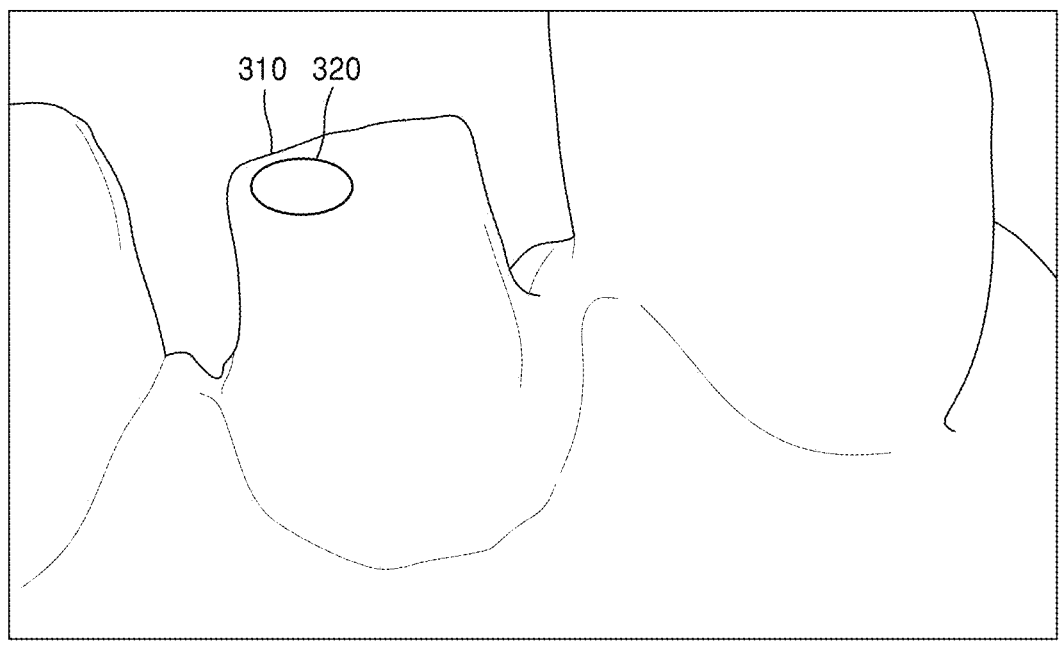
FIG. 3 illustrates a three-dimensional oral cavity model according to an embodiment.

FIG. 3 illustrates a three-dimensional oral cavity model according to an embodiment.

Referring to FIG. 3, the intraoral image processing apparatus 100 according to an embodiment may obtain three-dimensional intraoral data. For example, by scanning at least one tooth by using the intraoral scanner 1000 described in FIG. 1, intraoral data indicating surface information of an oral cavity may be obtained. The intraoral data according to an embodiment may include point data or mesh data. For example, the intraoral data may include position information of a point, the normal vector of a point, the tangent vector of a point, the normal vector of a mesh, position information of a mesh, and the like, but the disclosure is not limited thereto.

The intraoral image processing apparatus 100 may generate a three-dimensional oral cavity model 310, based on the intraoral data. In this state, the three-dimensional oral cavity model 310 may include a plurality of points, and triangular meshes constituted by the points. However, the disclosure is not limited thereto, and the three-dimensional oral cavity model may constituted by other polygonal meshes such as rectangles and the like.

The intraoral image processing apparatus 100 according to an embodiment may obtain roughness information of points included in a three-dimensional oral cavity model, based on the obtained intraoral data, which is described below in detail with reference to the accompanying drawings.

Figure 4:
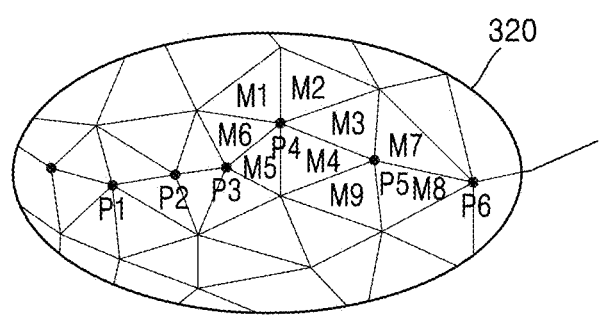
FIG. 4 is a reference view showing a method of obtaining curvature information about a three-dimensional oral cavity model, performed by an intraoral image processing apparatus according to an embodiment.
Figure 4:
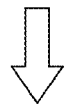
Figure 4:
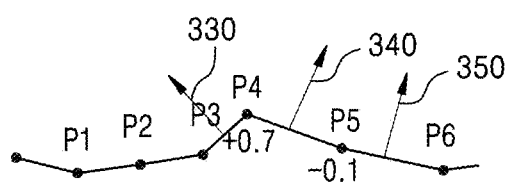
Figure 4:
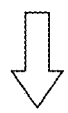
Figure 4:
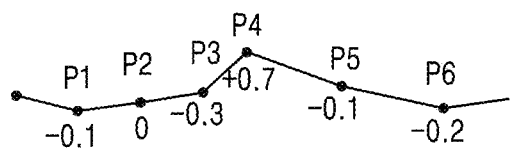

FIG. 4 is a reference view showing a method of obtaining curvature information about a three-dimensional oral cavity model, performed by an intraoral image processing apparatus according to an embodiment.

The intraoral image processing apparatus 100 according to an embodiment may obtain curvature information of points included in a three-dimensional oral cavity model.

A curvature is a value indicating a degree of curving of a curve or a curved surface. A curvature value of a certain point included in a three-dimensional oral cavity model may indicate a degree of curving of a curve determined on an object surface on which the point is located. In this state, curves passing through the point may have different curving degrees according to directions thereof. Accordingly, the intraoral image processing apparatus 100 may determine the largest one of curvature values of the point as a curvature value of the point, or an average value of the curvature values as a curvature value of the point. However, the disclosure is not limited thereto.

In FIG. 4, for convenience of explanation, a method of obtaining curvature values based on first to sixth points P1 to P6 of points included in a first region 320 of FIG. 3 is described.

The intraoral image processing apparatus 100 according to an embodiment may determine the sign of a curvature value of a point to be (+) when a curve or a curved surface passing through the point is convex, and to be (−) when a curve or a curved surface passing through the point is concave. For example, the intraoral image processing apparatus 100 may determine the sign of the curvature value of the fourth point P4 to be (+), and the sign of the curvature value of the fifth point P5 to be (−).

Furthermore, the intraoral image processing apparatus 100 may determine a magnitude of a curvature value of a point, by using normal vectors of meshes adjacent to the point. In this state, when a point and a mesh are adjacent to each other, it means that the mesh includes the point as a vertex. For example, the fourth point P4 may be adjacent to first to sixth meshes M1, M2, M3, M4, M5, and M6. Furthermore, the fifth point P5 may be adjacent to the third mesh M3, the fourth mesh M4, the seventh mesh M7, the eighth mesh M8, and the ninth mesh M9.

The intraoral image processing apparatus 100 may determine a magnitude of a curvature value of a point, based on a difference between at least two of the normal vectors of meshes adjacent to the point. In this state, the difference between normal vectors may be represented as an angle between the normal vectors. For example, the intraoral image processing apparatus 100 may determine a magnitude of a curvature value of the fourth point P4, based on an angle between a normal vector 330 of the sixth mesh M6 and a normal vector 340 of the third mesh M3. Furthermore, the intraoral image processing apparatus 100 may determine the magnitude of the curvature value of the fifth point P5, based on an angle between the normal vector 340 of the third mesh M3 and a normal vector 350 of the eighth mesh M8.

The intraoral image processing apparatus 100 may determine the curvature value of a point such that the magnitude of a curvature value increases as a difference between the normal vectors of adjacent meshes increases, and the magnitude of a curvature value decreases as the difference between the normal vectors of meshes decreases. For example, as the angle between the normal vector 330 of the sixth mesh M6 and the normal vector 340 of the third mesh M3, which are adjacent to the fourth point P4, is greater than the angel between the normal vector 340 of the third mesh M3 and the normal vector 350 of the eighth mesh M8, which are adjacent to the fifth point P5, the magnitude of the curvature value of the fourth point P4 may be determined to be greater than the magnitude of the curvature value of the fifth point P5. For example, the magnitude of the curvature value of the fourth point P4 may be determined to be 0.7, and the magnitude of the curvature value of the fifth point P5 may be determined to be −0.1.

Furthermore, in the same method, the curvature value of the first point P1 may be determined to be −0.1, the curvature value of the second point P2 may be determined to be 0, the curvature value of the third point P3 may be determined to be −0.3, and the curvature value of the sixth point P6 may be determined to be −0.2.

However, the disclosure is not limited thereto, and the intraoral image processing apparatus 100 according to an embodiment may determine the curvature values of points included in a three-dimensional oral cavity model in various methods. The intraoral image processing apparatus 100 may determine a magnitude of a curvature value of a point, based on the normal vectors of points included in a three-dimensional oral cavity model. For example, the intraoral image processing apparatus 100 may determine the magnitude of the curvature value of the fifth point P5, based on a difference between the normal vector of the fourth point P4 adjacent to the fifth point P5 and the normal vector of the sixth point P6 adjacent to the fifth point P5.

Furthermore, the intraoral image processing apparatus 100 according to an embodiment may determine the curvature values of points included in a three-dimensional oral cavity model, by using various well-known curvature calculation methods other than the above-described method.

Figure 5:
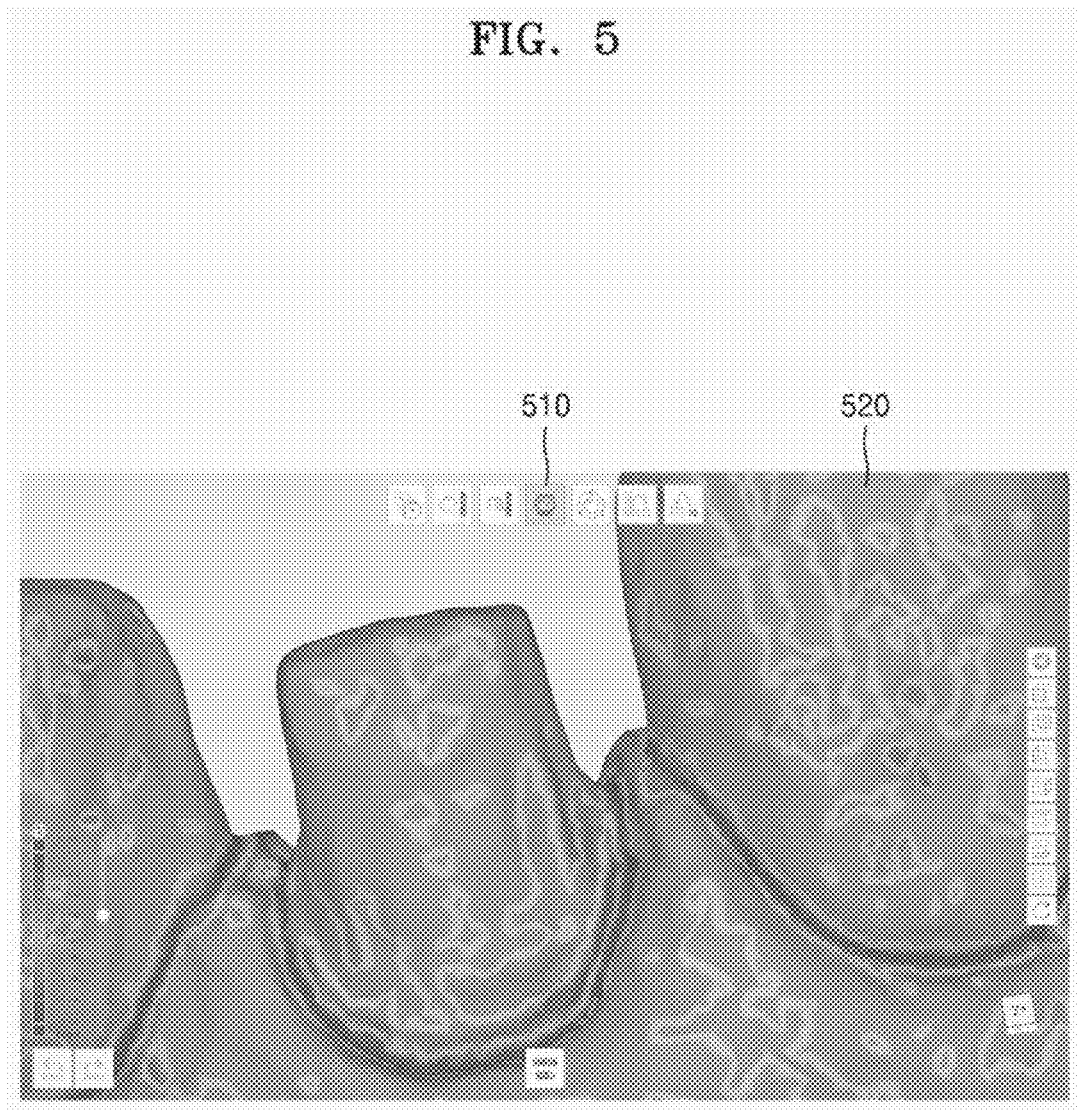
FIG. 5 illustrates an example in which an intraoral image processing apparatus according to an embodiment displays curvature information of a three-dimensional oral cavity model.

FIG. 5 illustrates an example in which an intraoral image processing apparatus according to an embodiment displays curvature information of a three-dimensional oral cavity model.

Referring to FIG. 5, the intraoral image processing apparatus 100 may display a curvature mode menu 510 for displaying curvature information of a three-dimensional oral cavity model on a user interface screen. When a user input to select the curvature mode menu 510 is received, the intraoral image processing apparatus 100 may display curvature information 520 of the three-dimensional oral cavity model in colors. For example, the intraoral image processing apparatus 100 may determine color of each point, based on a curvature value of each of points included in the three-dimensional oral cavity model. In this state, the intraoral image processing apparatus 100 may map each point with a color corresponding to the curvature value of each point, by using a color bar that represents the correspondence between a color and a curvature value. Furthermore, the intraoral image processing apparatus 100 may determine the color of a mesh by mixing the colors of points constituting the mesh. The intraoral image processing apparatus 100 may display the points included in the three-dimensional oral cavity model and meshes in the determined colors. For example, the intraoral image processing apparatus 100 may display a region having a relatively high curvature value in red, and a region having a relatively low curvature value in blue, in the three-dimensional oral cavity model. However, the disclosure is not limited thereto.

Figure 6:
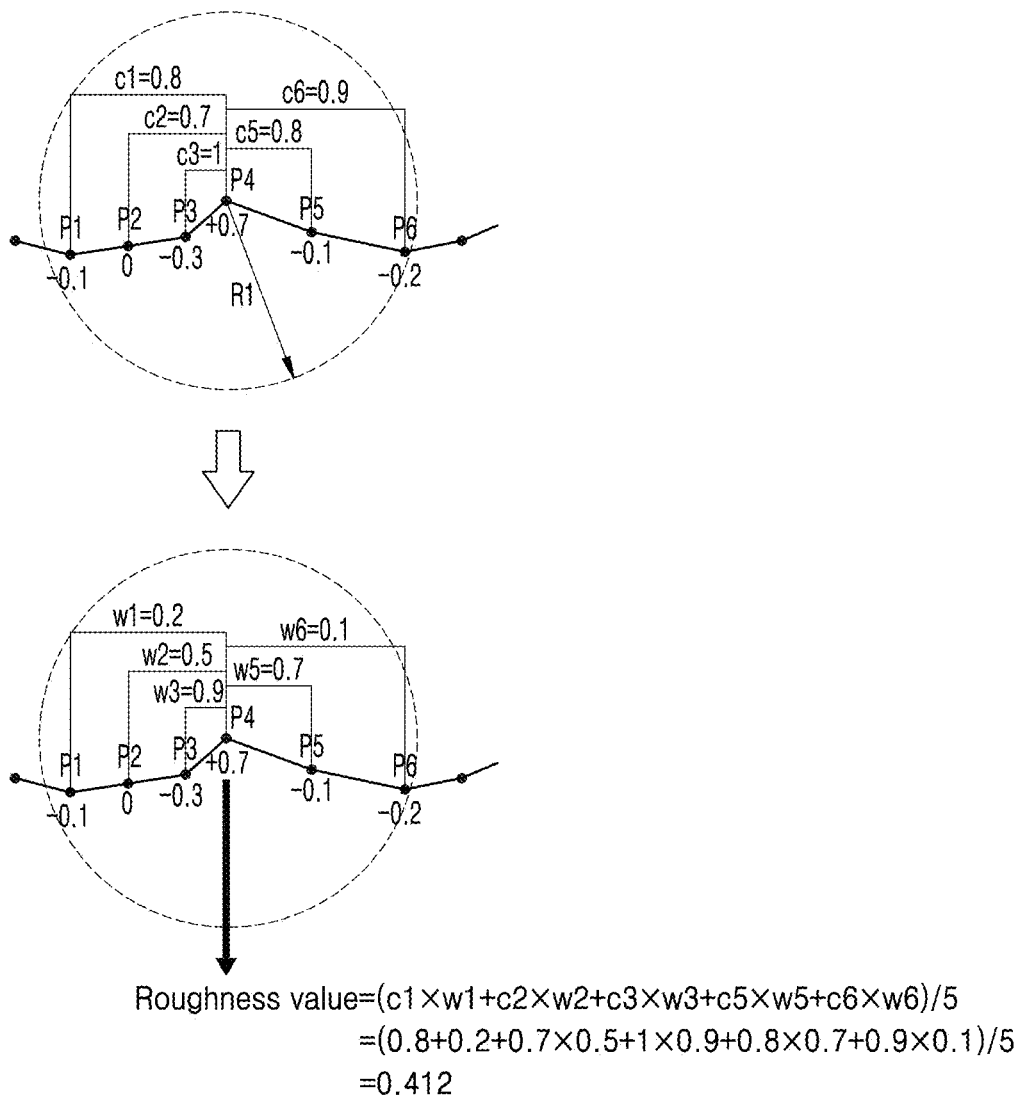
FIG. 6 is a reference view showing a method of obtaining roughness information of a three-dimensional oral cavity model, performed by an intraoral image processing apparatus according to an embodiment.

FIG. 6 is a reference view showing a method of obtaining roughness information of a three-dimensional oral cavity model, performed by an intraoral image processing apparatus according to an embodiment.

The intraoral image processing apparatus 100 according to an embodiment may obtain roughness information of points included in a three-dimensional oral cavity model, based on the curvature information. Roughness may be a value indicating a degree of irregularities in a vertical state of a surface. A roughness value of a point included in a three-dimensional oral cavity model, when comparing the curvature value of the point with curvature values of adjacent points, may be determined such that the roughness value increases as a difference thereof increases, and the roughness value decreases as the difference decreases.

In FIG. 6, a method of obtaining a roughness value based on the fourth point P4 is described.

Referring to FIG. 6, the intraoral image processing apparatus 100 according to an embodiment may calculate a difference between the curvature value of a point to calculate a roughness value and each of curvature values of points within a preset radius with respect to the point. For example, when the roughness value of the fourth point P4 is to be calculated, curvature values of points located within a radius R1, that is, the first point P1, the second point P2, the third point P3, the fifth point P5 and the sixth point P6, around the fourth point P4 may be used. In this state, while R1 may be 0.5 mm, this is merely exemplary, and R1 may have a different value.

The intraoral image processing apparatus 100 may calculate a difference C1, for example, 0.8, between the curvature value of the first point P1 and the curvature value of the fourth point P4, a difference C2, for example, 0.7, between the curvature value of the second point P2 and the curvature value of the fourth point P4, a difference C3, for example, 1, between the curvature value of the third point P3 and the curvature value of the fourth point P4, a difference C5, for example, 0.8, between the curvature value of the fifth point P5 and the curvature value of the fourth point P4, and a difference C6, for example, 0.9, between the curvature value of the sixth point P6 and the curvature value of the fourth point P4.

The intraoral image processing apparatus 100 may calculate an average value by applying a weight to each of the calculated difference values. In this state, a weight applied to each of the difference values may be determined inversely proportional to a distance between points. For example, the intraoral image processing apparatus 100 may determine a weight to a difference between the curvature value of a point to calculate a roughness value and the curvature of a point close to the point, to be great, and a weight to a difference between the curvature value of the point to calculate the roughness value and the curvature of a point far from the point, to be less.

For example, the intraoral image processing apparatus 100 may apply a greatest weight W3, for example, 0.9, to a difference C3, for example, 1, between the curvature value of the fourth point P4 and the curvature value of the third point P3 that is closest to the fourth point P4, and a least weight W6, for example, 0.1, to a difference C6, for example, 0.9, between the curvature value of the fourth point P4 and the curvature value of the sixth point P6 that is farthest from the fourth point P4. However, the above figures are merely exemplary, and weights of various sizes may be applied thereto.

When weights are determined, the intraoral image processing apparatus 100 may calculate an average value, for example, 0.412, by applying a weight to the calculated each of the difference values. The calculated average value may be determined as the roughness value of the fourth point P4.

The intraoral image processing apparatus 100 may determine a roughness value of each of the points included in a three-dimensional oral cavity model by the method described above.

Figure 7:
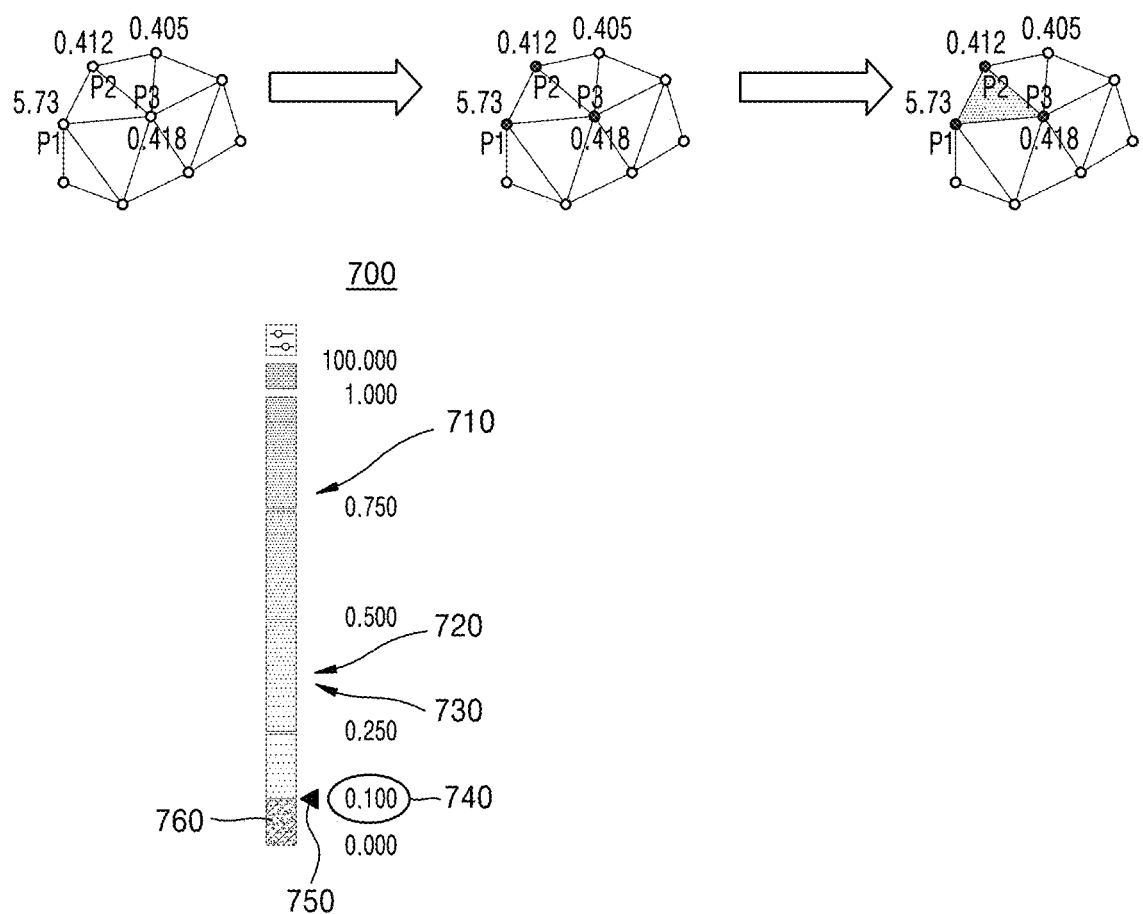
FIG. 7 is a reference view showing a method of determining a roughness color, performed by an intraoral image processing apparatus according to an embodiment.

FIG. 7 is a reference view showing a method of determining a roughness color, performed by an intraoral image processing apparatus according to an embodiment.

Referring to FIG. 7, the intraoral image processing apparatus 100 according to an embodiment may determine roughness color of each point, based on the roughness value of each of the points included in a three-dimensional oral cavity model. The intraoral image processing apparatus 100 may map a color corresponding to the roughness value of each point with each point by using a color bar 700. For example, when the roughness value of the first point P1 is 5.73, the intraoral image processing apparatus 100 may determine a first color 710 corresponding to 5.73 in the color bar 700 as the roughness color of the first point P1. Furthermore, when the roughness value of the second point P2 is 0.412, a second color 730 corresponding to 0.412 in the color bar 700 may be determined as the roughness color of the second point P2. Furthermore, when the roughness value of the third point P3 is 0.418, a third color 720 corresponding to 0.418 in the color bar 700 as the roughness color of the third point P3.

The color bar 700 according to an embodiment may be set to map a higher roughness value with redder, and a lower roughness value with greener, but the disclosure is not limited thereto. Furthermore, the intraoral image processing apparatus 100 may change the color mapped in the color bar 700 and a range of a roughness value mapped with a certain color. For example, the intraoral image processing apparatus 100 may change the range of a roughness value mapped with a fourth color 760, for example, green, in the color bar 700, based on a user input to vertically move a user input or a triangular icon 750 that directly inputs a first numerical value 740.

Furthermore, when the roughness colors of the first to third points P1, P2, and P3 are determined, the intraoral image processing apparatus 100 according to an embodiment may determine the color of a first triangular mesh M1 constituted by the first to third points P1, P2, and P3. For example, the intraoral image processing apparatus 100 may determine the roughness color of the first triangular mesh M1 by mixing the roughness colors of the first to third points P1, P2, and P3. In this state, the first triangular mesh M1 may be represented in a single color or in a gradation of a plurality of colors. However, the disclosure is not limited thereto.

Figure 8:
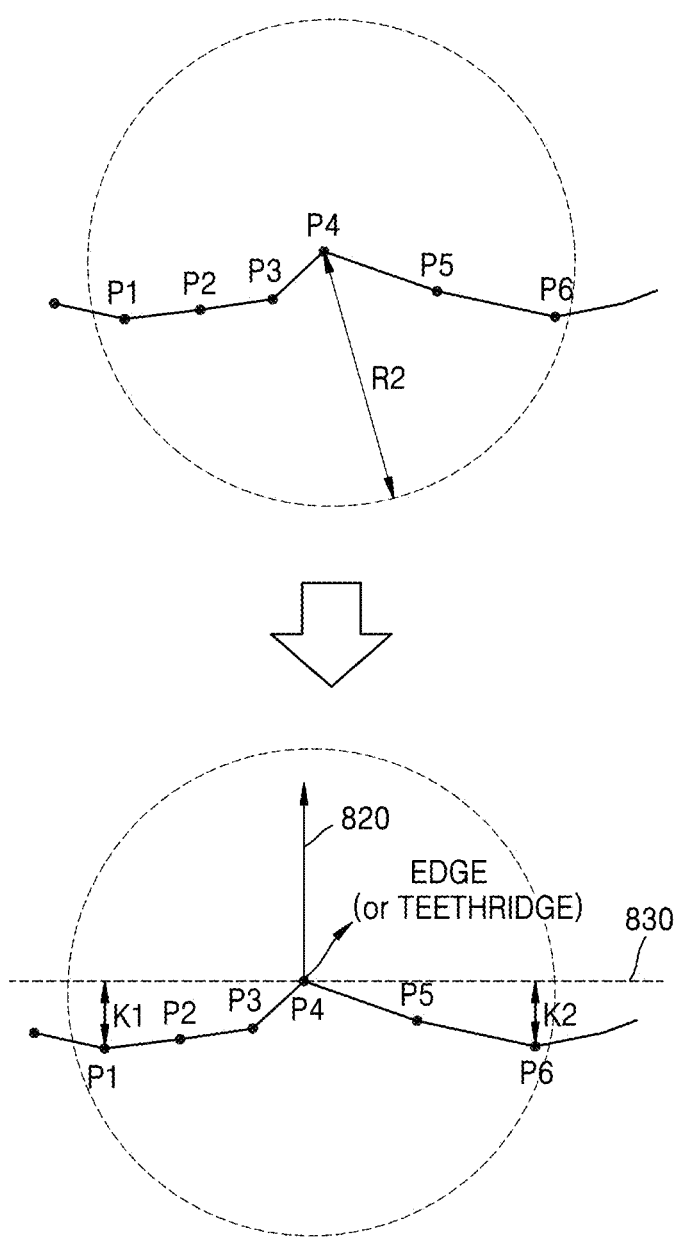
FIG. 8 is a reference view showing a method of detecting an edge or teethridge from a three-dimensional oral cavity model, performed by an intraoral image processing apparatus according to an embodiment.

FIG. 8 is a reference view showing a method of detecting an edge or teethridge from a three-dimensional oral cavity model, performed by an intraoral image processing apparatus according to an embodiment.

In a three-dimensional oral cavity model obtained by modeling an oral cavity, a teethridge region that is a boundary between teeth and gum or an area of an edge of a tooth may appear to have a large curvature value due to the shape and structure thereof. The teethridge region means a teethridge or an area adjacent to the teethridge, and the edge region means an edge or an area adjacent to the edge.

As the curvature value of a teethridge region or an edge region appears to be relatively large, the roughness values of the corresponding regions may always appear to be large. Accordingly, when the roughness information of a three-dimensional oral cavity model is provided to check the prep state, the intraoral image processing apparatus 100 may process the roughness values of a teethridge region or an edge region to be 0 or a preset value. For example, when the roughness value of a teethridge region or an edge region appears to be high, it may be understood that the corresponding area needs an additional prep operation.

The intraoral image processing apparatus 100 according to an embodiment may detect a teethridge region or an edge region in a three-dimensional oral cavity model. In the following description, a method of determined whether a certain point is a point located in a teethridge region or an edge region is described with reference to FIG. 8.

The intraoral image processing apparatus 100 may determine whether the fourth point P4 is a point located in a teethridge region or an edge region. The intraoral image processing apparatus 100 may detect two reference points located at the outermost side among the points located within a preset radius R2 with respect to the fourth point P4. For example, the intraoral image processing apparatus 100 may detect the first point P1 and the sixth point P6 as reference points.

The intraoral image processing apparatus 100 may measure a distance k1 between a tangent line 830 of a normal vector 820 of the fourth point P4 and the first point P1 and a distance k2 between the tangent line 830 of the normal vector 820 of the fourth point P4 and the sixth point P6, and when the average value of k1 and k2 is a preset threshold value or more, determine the fourth point P4 to be located in a teethridge region or an edge region.

The intraoral image processing apparatus 100 according to an embodiment may set the roughness values of points located in a teethridge region or an edge region to be 0 or a preset value.

Figure 9:
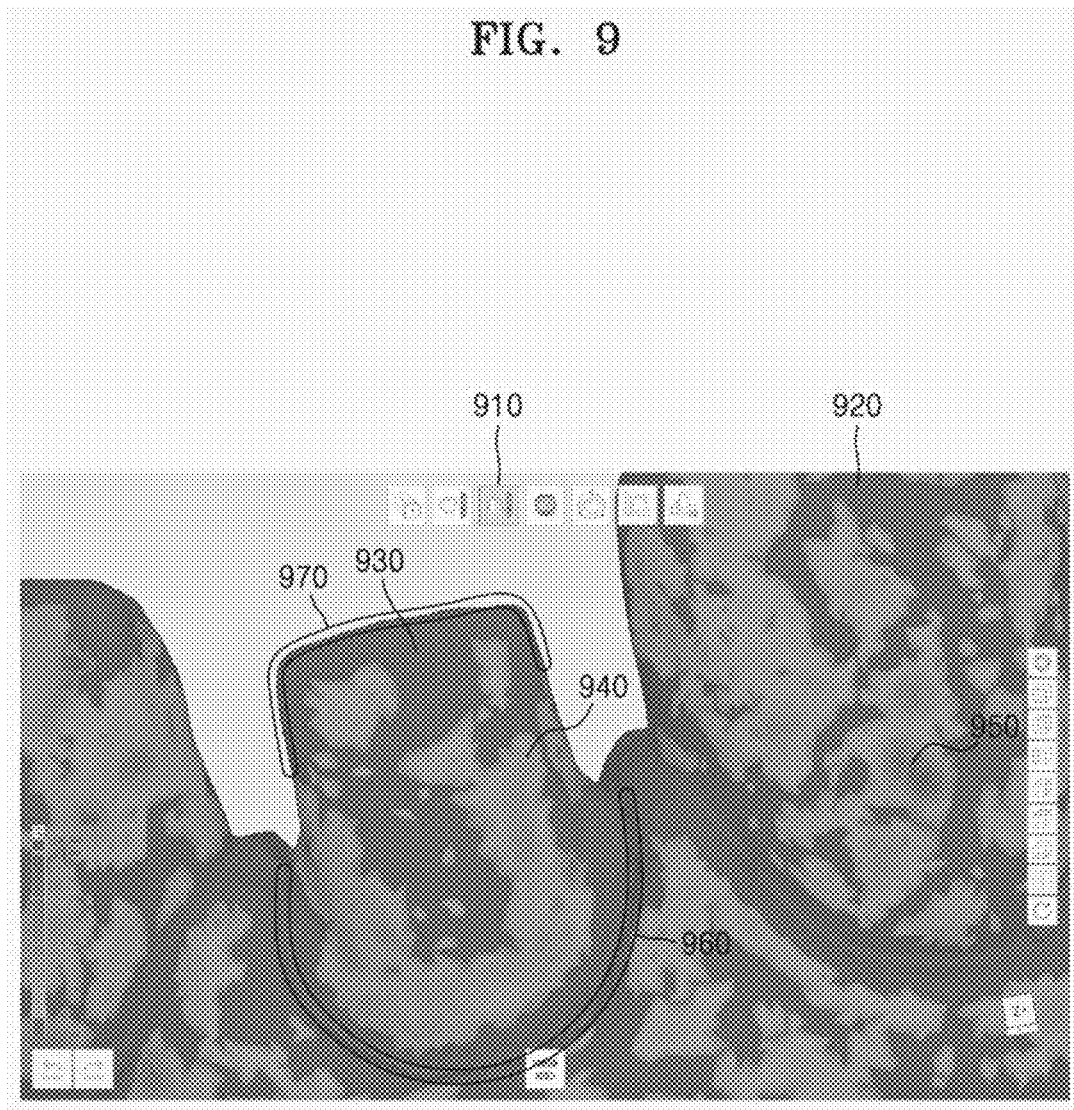
FIG. 9 illustrates an example in which an intraoral image processing apparatus according to an embodiment displays roughness information of a three-dimensional oral cavity model.

FIG. 9 illustrates an example in which an intraoral image processing apparatus according to an embodiment displays roughness information of a three-dimensional oral cavity model.

Referring to FIG. 9, the intraoral image processing apparatus 100 may display a roughness mode menu 910 to display the roughness information of a three-dimensional oral cavity model on a user interface screen. When a user input to select the roughness mode menu 910 is received, the intraoral image processing apparatus 100 may display roughness information 920 of the three-dimensional oral cavity model, in colors. For example, as described and illustrated in FIG. 7, when the roughness colors of points and meshes included in the three-dimensional oral cavity model are determined, the points and meshes may be displayed in the determined colors. In this state, a region having a small roughness value may be displayed in a first color 930, for example, green, and a region displayed in the first color 930 may indicate a region that does not need an additional prep operation. In contrast, a region having a great roughness value may be displayed in a second color 940, for example, yellow, or a third color 950, for example, red, and a region displayed in the second color 940 or the third color 950 may indicate a region that needs an additional prep operation.

Furthermore, as described and illustrated in FIG. 8, the roughness values of points and meshes located in the teethridge region or edge regions of a tooth may be set to be 0 or a preset value. In this state, 0 or the preset value may be mapped with the first color 930, and as illustrated in FIG. 9, a teethridge region 960 or an edge region 970 may be displayed in the first color, for example, green, that indicates a region that does not need an additional prep operation.

Figure 10:
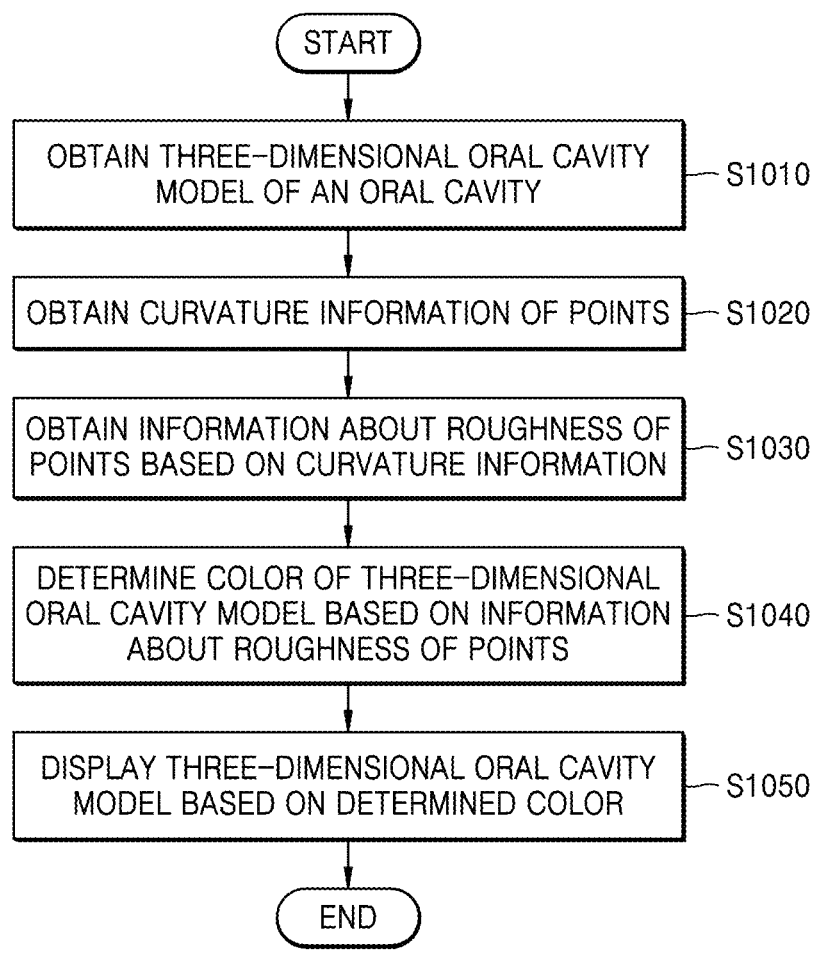
FIG. 10 is a flowchart showing an intraoral image processing method according to an embodiment.

FIG. 10 is a flowchart showing an intraoral image processing method according to an embodiment.

Referring to FIG. 10, the intraoral image processing apparatus 100 according to an embodiment may obtain intraoral data and a three-dimensional oral cavity model, based on the intraoral data (S1010).

Intraoral data may be obtained by scanning at least one tooth by using the intraoral scanner 1000. In this state, not only a tooth, but also gingiva close to the tooth may be scanned together. The intraoral data according to an embodiment may be point data or mesh data, and may be data indicating information about a surface of an oral cavity. For example, the intraoral data may include position information of a point, the normal vector of a point, the tangent vector of a point, the normal vector of a mesh, position information of a mesh, and the like, but the disclosure is not limited thereto.

Furthermore, the intraoral image processing apparatus 100 may generate a three-dimensional oral cavity model, based on the intraoral data. In this state, the three-dimensional oral cavity model may include a plurality of points, and triangular meshes constituted by the points. However, the disclosure is not limited thereto, and the three-dimensional oral cavity model may be constituted by other polygonal meshes such as rectangles and the like.

The intraoral image processing apparatus 100 according to an embodiment may obtain curvature information of points included in the three-dimensional oral cavity model (S1020).

A curvature value of a certain point included in a three-dimensional oral cavity model may represent a degree of curving of a curve determined on an object surface where the point is located. The intraoral image processing apparatus 100 may determine the sign of a curvature value of the point to be (+) when a curve or a curved surface passing through the point is convex, and the sign of a curvature value of the point to be (−) when a curve or a curved surface passing through the point is concave.

Furthermore, the intraoral image processing apparatus 100 may determine a magnitude of a curvature value of a point by using the normal vectors of meshes adjacent to the point. The intraoral image processing apparatus 100 may determine a magnitude of a curvature value of the point, based on a difference between at least two of the normal vectors of meshes adjacent to the point. In this state, the difference between the normal vectors may be represented as an angle between the normal vectors. The intraoral image processing apparatus 100 may determine a magnitude of a curvature value of a point such that the magnitude of a curvature value increases as the angle between the normal vectors of adjacent meshes increases, and the magnitude of a curvature value decreases as the angle between the normal vectors of meshes decreases. As the method of determining the curvature value of a point is described in detail with reference to FIG. 4, a detailed description thereof is omitted.

The intraoral image processing apparatus 100 according to an embodiment may obtain roughness information of points included in the three-dimensional oral cavity model, based on curvature information (S1030).

Roughness may be a value indicating a degree of irregularities in a vertical state of a surface. The intraoral image processing apparatus 100 may determine a roughness value to be large when a difference is large, and a roughness value to be small when a difference is small, by comparing the curvature value of a point included in a three-dimensional oral cavity model with the curvature values of adjacent points. As the method of calculating a roughness value of a point is described in detail with reference to FIG. 6, a detailed description thereof is omitted.

The intraoral image processing apparatus 100 according to an embodiment may determine the color of the three-dimensional oral cavity model, based on information about roughness of points (S1040).

The intraoral image processing apparatus 100 according to an embodiment may determine the roughness color of each point, based on the roughness value of each of the points included in the three-dimensional oral cavity model. For example, the intraoral image processing apparatus 100 may map a color corresponding to the roughness value of each point with each point by using a color bar. Furthermore, when the roughness colors of points are determined, the intraoral image processing apparatus 100 may determine the roughness color of a mesh, by mixing the roughness colors of points constituting the mesh. As this is described in detail with reference to FIG. 7, a detailed description thereof is omitted.

Furthermore, the intraoral image processing apparatus 100 according to an embodiment may set the roughness value of a teethridge or an edge region of a tooth to be 0 or a preset value, and determine the roughness color as a first color, for example, green, by detecting a teethridge region that is a boundary between the tooth and gum or an edge region of the tooth, in the three-dimensional oral cavity model.

The intraoral image processing apparatus 100 according to an embodiment may display the three-dimensional oral cavity model, based on the determined color (S1050).

The intraoral image processing apparatus 100 may display the roughness information of the three-dimensional oral cavity model in colors, based on the user input to select a roughness mode. For example, in operation 1040 (S1040), when the roughness colors of points and meshes included in the three-dimensional oral cavity model are determined, the intraoral image processing apparatus 100 may display the points and meshes in the determined colors.

Figure 11:
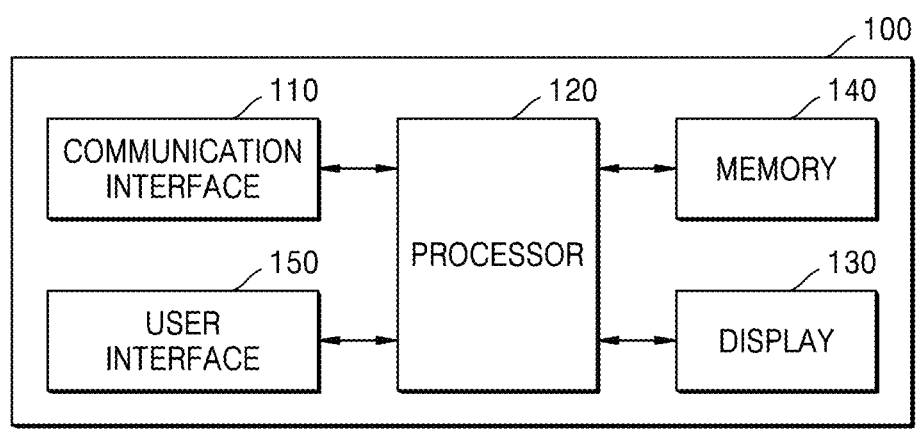
FIG. 11 is a block diagram of an intraoral image processing apparatus according to an embodiment.

FIG. 11 is a block diagram of the intraoral image processing apparatus 100 according to an embodiment.

The intraoral image processing method of FIG. 10 may be performed by the intraoral image processing apparatus 100. Accordingly, the intraoral image processing method of FIG. 10 may be a flowchart showing the operations of the intraoral image processing apparatus 100.

Referring to FIG. 11, the intraoral image processing apparatus 100 may include a communication interface 110, a user interface 150, the display 130, a memory 140, and a processor 120.

The communication interface 110 may perform communication with at least one external electronic apparatus, for example, the intraoral scanner 1000, a server, an external medical apparatus, or the like, via a wired or wireless communication network. The communication interface 110 may perform communication with at least one external electronic apparatus under the control of the processor 120.

In detail, the communication interface 110 may include at least one short-range communication module that performs communication according to communication standards, such as Bluetooth, Wi-Fi, Bluetooth low energy (BLE), NFC/RFID, Wi-Fi Direct, UWB, ZIGBEE, or the like.

Furthermore, the communication interface 110 may further include a long-range communication module that performs communication with a server for supporting a long-range communication according to long-range communication standards. In detail, the communication interface 110 may further include a long-range communication module that performs communication via a network for the Internet communication. Furthermore, the communication interface 110 may include a long-range communication module that performs communication via a communication network according to communication standards for 3G, 4G, 5G, and/or the like.

Furthermore, the communication interface 110 may include at least one port to be connected to an external electronic apparatus by a wired cable, to communicate with an external electronic apparatus, for example, an intraoral scanner and the like, by wire. Accordingly, the communication interface 110 may perform communication with an external electronic apparatus that is connected by wire through at least one port.

The user interface 150 may receive a user input to control the intraoral image processing apparatus 100. The user interface 150 may include user input devices including a touch panel for sensing a touch by a user, a button for receiving a push manipulation by a user, a mouse or keyboard for assigning or selecting a point on a user interface screen, and the like, but the disclosure is not limited thereto.

Furthermore, the user interface 150 may include a voice recognition apparatus for voice recognition. For example, the voice recognition apparatus may be a microphone, and the voice recognition apparatus may receive voice commands or voice requests by a user. Accordingly, the processor 120 may control performing of operations corresponding to the voice commands or voice requests.

The display 130 displays a screen. In detail, the display 130 may display a certain screen under the control of the processor 120. In detail, the display 130 may display a user interface screen including an intraoral image generated based on the data obtained by scanning patient's oral cavity using the intraoral scanner 1000. Alternatively, the display 130 may display a user interface screen including information related to patient's dental treatment.

The memory 140 may store at least one instruction. Furthermore, the memory 140 may store at least one instruction to be executed by the processor 120. Furthermore, the memory 140 may store at least one program to be executed by the processor 120. Furthermore, the memory 140 may store data received from the intraoral scanner 1000, for example, raw data and the like obtained through the oral cavity scanning. Alternatively, the memory 140 may store an intraoral image that represents an oral cavity three-dimensionally (a three-dimensional oral cavity model). The memory 140 according to an embodiment may include one or more instructions to provide roughness information of a three-dimensional oral cavity model. The memory 140 according to an embodiment may include one or more instructions to perform the method disclosed in the specification to provide roughness information of a three-dimensional oral cavity model.

The processor 120 may control performing of a desired operation by executing at least one instruction stored in the memory 140. The at least one instruction may be stored in an internal memory included in the processor 120 or the memory 140 included in a data processing apparatus, aside from the processor 120.

In detail, the processor 120 may control at least one of components included in the data processing apparatus to perform a desired operation, by performing at least one instruction. Accordingly, when the processor 120 performs certain operations, the processor 120 controls at least one of components included in the data processing apparatus to perform certain operations.

According to an embodiment the processor 120, by executing one or more instruction stored in the memory 140, may obtain intraoral data by scanning at least one tooth. The intraoral data according to an embodiment may be point data or mesh data, and may be data indicating information about a surface of an oral cavity. For example, the intraoral data may include position information of a point, the normal vector of a point, the tangent vector of a point, the normal vector of a mesh, position information of a mesh, and the like, but the disclosure is not limited thereto.

Furthermore, the processor 120, by executing one or more instruction stored in the memory 140, may generate a three-dimensional oral cavity model, based on the intraoral data. In this state, the three-dimensional oral cavity model may include a plurality of points, and meshes constituted by the points.

Furthermore, the processor 120, by executing one or more instruction stored in the memory 140, may obtain curvature information of points included in a three-dimensional oral cavity model. As the method of determining a curvature value of a certain point included in a three-dimensional oral cavity model is described in detail with reference to FIG. 4, a detailed description thereof is omitted.

The processor 120, by executing one or more instruction stored in the memory 140, may obtain roughness information of points included in a three-dimensional oral cavity model, based on the curvature information. The processor 120 may determine a roughness value to be large when a difference is large, and a roughness value to be small when a difference is small, by comparing the curvature value of a point included in a three-dimensional oral cavity model with the curvature values of adjacent points. As the method of calculating the roughness value of a point is described in detail with reference to FIG. 6, a detailed description thereof is omitted.

The processor 120, by executing one or more instruction stored in the memory 140, may determine the color of a three-dimensional oral cavity model, based on the information about roughness of points. For example, the processor 120 may map a color corresponding to the roughness value of each point with each point, by using a color bar. Furthermore, the processor 120 may determine the roughness color of a mesh, by mixing the roughness colors of points constituting the mesh.

The processor 120, by executing one or more instruction stored in the memory 140, may set the roughness value of a teethridge or an edge region of a tooth to be 0 or a preset value, and determine the roughness color as a first color, for example, green, by detecting a teethridge region that is a boundary between a tooth and gum or an edge region of a tooth, in a three-dimensional oral cavity model.

The processor 120, by executing one or more instruction stored in the memory 140, may control the display 130 to display a three-dimensional oral cavity model, based on the determined roughness color.

The processor 120 according to an embodiment may be implemented in the form including internally at least one internal processor and a memory device, for example, RAM, ROM, and the like, for storing at least one of a program, an instruction, a signal, data, and the like to be used or processed in the internal processor.

Furthermore, the processor 120 may include a graphics processing unit processor for graphics process corresponding to video. Furthermore, the processor 120 may be implemented as a system-on-chip (SoC) incorporating a core and a GPU. Furthermore, the processor 120 may include a multi core more than a single core. For example, the processor 120 may include a dual core, a triple core, a quad core, a hexa core, an octa core, a deca core, a dodeca core, a hexadeca core, and the like.

In the disclosed embodiment, the processor 120 may generate an intraoral image, based on the two-dimensional image received from the intraoral scanner 1000.

In detail, under the control of the processor 120, the communication interface 110 may receive the data obtained by the intraoral scanner 1000, for example, raw data obtained through the oral cavity scanning. The processor 120 may generate a three-dimensional intraoral image that represents an oral cavity three-dimensionally, based on the raw data received from the communication interface 110. For example, the intraoral scanner 1000 may include an L camera corresponding to the left field of view and an R camera corresponding to the right field of view, to reconstruct a three-dimensional image according to an optical triangulation method. The intraoral scanner 1000 may obtain L image data corresponding to the left field of view and R image data corresponding to the right field of view, respectively from the L camera and the R camera. Next, the intraoral scanner 1000 may transmit raw data including the L image data and the R image data to the communication interface 110 of the intraoral image processing apparatus 100.

Then, the communication interface 110 may transmit the received raw data to the processor 120, and the processor 120 may generate an intraoral image that represents an oral cavity three-dimensionally, based on the received raw data.

Furthermore, the processor 120 may receive an intraoral image that represents an oral cavity three-dimensionally directly from an external server, a medical apparatus, and the like, by controlling the communication interface 110. In this case, the processor 120 may obtain a three-dimensional intraoral image, without generating a three-dimensional intraoral image based on the raw data.

According to the disclosed embodiment, the performing of operations such as "extraction," "obtaining," "generating," and the like, by the processor 120, may include not only directly performing the above-described operations by executing at least one instruction in the processor 120, but also controlling other constituent elements to perform the above-described operations.

In order to implement the embodiments disclosed in the specification, the intraoral image processing apparatus 100 may include only some of the constituent elements illustrated in FIG. 11, or more constituent elements other than the constituent elements illustrated in FIG. 11.

Furthermore, the intraoral image processing apparatus 100 may store and execute dedicated software in conjunction with the intraoral scanner 1000. The dedicated software may be referred to as a dedicated program, a dedicated tool, or a dedicated application. When the intraoral image processing apparatus 100 operates in conjunction with the intraoral scanner 1000, the dedicated software stored in the intraoral image processing apparatus 100 may be connected to the intraoral scanner 1000 to receive, in real time, data obtained through the oral cavity scanning. For example, dedicated software for processing data obtained through oral cavity scanning exists for a product "i500" that is an intraoral scanner by Medit. In detail, Medit manufactures and distributes "Medit Link" that is software for processing, managing, using, and/or transmitting data obtained by an intraoral scanner, for example, i500. The "dedicated software" means a program, a tool, or an application capable of operating in conjunction with an intraoral scanner, and various intraoral scanners that are developed and sold by various manufacturers may be commonly used. Furthermore, the above-described dedicated software may be manufactured and distributed separate from an intraoral scanner that performs oral cavity scanning.

The intraoral image processing apparatus 100 may store and execute dedicated software corresponding to the product i500. Transmission software may perform at least one of operations to obtain, process, store, and/or transmit an intraoral image. The dedicated software may be stored in the processor 120. Furthermore, the dedicated software may provide a user interface for use of data obtained from an intraoral scanner. A user interface screen provided by the dedicated software may include an intraoral image generated according to the disclosed embodiment.

The intraoral image processing method according to an embodiment may be implemented in the form of a program command to be executed through various computer devices and recorded on a computer-readable medium. Furthermore, the embodiment of the disclosure may include a computer-readable storage medium having recorded thereon one or more programs including at least one instruction to execute an intraoral image processing method.

The computer-readable storage medium may include a program command, a data file, a data structure, and the like alone or in combination. Examples of a computer-readable storage medium may include magnetic media such as hard disks, floppy disks, and magnetic tapes, optical recording media such as CD-ROMs and DVDs, and magneto-optical media such as floppy disks, and hardware devices configured to store and execute program commands, such as ROM, RAM, and flash memory.

A machine-readable storage medium may be provided in the form of a non-transitory storage medium. The non-transitory may mean that a storage medium is a tangible device. Furthermore, the "non-transitory storage medium" may include a buffer for temporarily storing data.

According to an embodiment, the intraoral image processing methods according to various embodiments of the disclosure may be provided by being included in a computer program product. The computer program product may be distributed in the form of a machine-readable storage medium, for example, CD-ROM. Alternatively, the computer program product may be distributed (e.g., download or upload) directly or online between two user devices (e.g., smartphones) through an application store (e.g., PlayStore™) or through two user devices (e.g., smartphones). In detail, the computer program product according to an embodiment may include a storage medium having recorded thereon a program including at least one instruction for performing the intraoral image processing method according to the disclosed embodiment.

The intraoral image processing apparatus, and the intraoral image processing method, according to the embodiments of the disclosure may provide roughness information about a three-dimensional oral cavity model, considering the geometrical structure of an oral cavity. Accordingly, by using the provided roughness information, it is possible to perform a prep operation to cut a tooth in the form of an abutment, and thus, the time required for the prep operation may be reduced and the accuracy of the prep operation may be increased.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. An intraoral image processing method comprising:
    obtaining a three-dimensional oral cavity model of an oral cavity;
    obtaining curvature information including curvature values of a plurality of points included in the three-dimensional oral cavity model;
    obtaining roughness information including roughness values of the plurality of points included in the three-dimensional oral cavity model, based on the curvature information;
    obtaining a color of the three-dimensional oral cavity model, based on the roughness information; and
    displaying the three-dimensional oral cavity model, based on the obtained color,
    wherein the obtaining of the roughness information comprises:
    determining at least one point included in a teethridge region being a boundary between a teeth and a gum, and
    determining roughness value of the at least one point to be 0.

2. The intraoral image processing method of claim 1, wherein the obtaining of the roughness information comprises determining a roughness value of a first point included in the three-dimensional oral cavity model, based on a curvature value of at least one second point adjacent to the first point among the points.

3. The intraoral image processing method of claim 1, wherein the obtaining of the roughness information comprises determining a roughness value of a first point included in the three-dimensional oral cavity model, based on a value of a difference between a curvature value of at least one second point adjacent to the first point among the points and a curvature value of the first point.

4. The intraoral image processing method of claim 1, wherein the obtaining of the roughness information comprises:
    calculating a value of a difference between a curvature value of each of second points located within a preset first distance from a first point among the points included in the three-dimensional oral cavity model and a curvature value of the first point;
    determining a weight of the difference value, based on a distance between the first point and each of the second points; and
    determining a roughness value of the first point, based on the difference values and the weights with respect to the second points.

5. The intraoral image processing method of claim 4, wherein the determining of the roughness value of the first point comprises calculating an average value of the difference values, based on the weights; and determining the calculated average value as a roughness value of the first point.

6. The intraoral image processing method of claim 1, wherein the obtaining of the roughness information comprises determining the roughness values of the points included in the three-dimensional oral cavity model such that roughness values of the points increase as surfaces of the three-dimensional oral cavity model on which the points are located become increasingly rough, and roughness values of the points decrease as the surfaces of the three-dimensional oral cavity model on which the points are located become increasingly smooth.

7. The intraoral image processing method of claim 1, wherein the obtaining of the roughness information further comprises determining roughness values of points included in an edge region of a tooth, to be preset values.

8. The intraoral image processing method of claim 1, wherein the obtaining of the roughness information comprises:
determining whether a first point among the points included in the three-dimensional oral cavity model is included in an edge region of a tooth or the teethridge region, based on a distance between a tangent line of the first point and each of a third point farthest from the first point in a first direction and a fourth point farthest from the first point in a second direction among points located within a preset second distance from the first point; and
when the first point is included in the edge region of the tooth or the teethridge region, determining the roughness value of the first point to be 0.

9. The intraoral image processing method of claim 1, wherein the obtaining of the color of the three-dimensional oral cavity model comprises:
determining a color of a point according to the roughness value of each of the points included in the three-dimensional oral cavity model; and
determining a color of a mesh constituted by the points, by mixing colors of the points.

10. An intraoral image processing apparatus comprising:
a display;
a memory storing one or more instructions; and
a processor,
wherein the processor is configured to, by executing the one or more instructions stored in the memory:
obtain a three-dimensional oral cavity model of an oral cavity;
obtain curvature information including curvature values of a plurality of points included in the three-dimensional oral cavity model;
obtain roughness information including roughness values of the plurality of points included in the three-dimensional oral cavity model, based on the curvature information;
determine at least one point included in a teethridge region being a boundary between a teeth and a gum;
determine roughness value of the at least one point to be 0;
obtain a color of the three-dimensional oral cavity model, based on the roughness information; and
control the display to display the three-dimensional oral cavity model, based on the obtained color.

11. The intraoral image processing apparatus of claim 10, wherein the processor is further configured to, by executing the one or more instructions stored in the memory, determine a roughness value of the first point included in the three-dimensional oral cavity model, based on a curvature value of at least one second point adjacent to the first point among the points.

12. The intraoral image processing apparatus of claim 10, wherein the processor is further configured to, by executing the one or more instructions stored in the memory, determine a roughness value of a first point included in the three-dimensional oral cavity model, based on a value of a difference between a curvature value of at least one second point adjacent to the first point among the points and a curvature value of the first point.

13. The intraoral image processing apparatus of claim 10, wherein the processor is further configured to, by executing the one or more instructions stored in the memory:
calculate a value of a difference between a curvature value of each of second points located within a preset first distance from a first point among the points included in the three-dimensional oral cavity model and a curvature value of the first point;
determine a weight of the difference value, based on a distance between the first point and each of the second points; and
determine a roughness value of the first point, based on the difference values and the weights with respect to the second points.

14. The intraoral image processing apparatus of claim 13, wherein the processor is further configured to, by executing the one or more instructions stored in the memory, calculate an average value of the difference values, based on the weights; and determine the calculated average value as a roughness value of the first point.

15. The intraoral image processing apparatus of claim 10, wherein the processor is further configured to, by executing the one or more instructions stored in the memory, determine the roughness values of the points included in the three-dimensional oral cavity model such that roughness values of the points increase as surfaces of the three-dimensional oral cavity model on which the points are located become increasingly rough, and roughness values of the points decrease as the surfaces of the three-dimensional oral cavity model on which the points are located become increasingly smooth.

16. The intraoral image processing apparatus of claim 10, wherein the processor is further configured to, by executing the one or more instructions stored in the memory, determine roughness values of points included in an edge region of a tooth to be preset values.

17. The intraoral image processing apparatus of claim 10, wherein the processor is further configured to, by executing the one or more instructions stored in the memory:
determine whether a first point among the points included in the three-dimensional oral cavity model is included in an edge region of a tooth or the teethridge region, based on a distance between a tangent line of the first point and each of a third point farthest from the first point in a first direction and a fourth point farthest from the first point in a second direction among points located within a preset second distance from the first point; and
when the first point is included in the edge region of the tooth or the teethridge region, determine the roughness value of the first point to be 0.

18. The intraoral image processing apparatus of claim 10, wherein the processor is further configured to, by executing the one or more instructions stored in the memory:
determine a color of a point according to the roughness value of each of the points included in the three-dimensional oral cavity model; and
determine a color of a mesh constituted by the points, by mixing colors of the points.

* * * * *